US009664607B2

United States Patent
Park

(10) Patent No.: US 9,664,607 B2
(45) Date of Patent: May 30, 2017

(54) PORTABLE APPARATUS FOR ESTIMATING AIR QUALITY AND METHODS OF OPERATING THE SAME

(71) Applicant: Seoul Viosys Co., Ltd., Ansan-si (KR)

(72) Inventor: Stella Park, Ansan-si (KR)

(73) Assignee: SEOUL VIOSYS CO., LTD., Ansan-si (KR)

( * ) Notice: Subject to any disclaimer, the term of this patent is extended or adjusted under 35 U.S.C. 154(b) by 23 days.

(21) Appl. No.: 14/556,067

(22) Filed: Nov. 28, 2014

(65) Prior Publication Data

US 2015/0153275 A1 Jun. 4, 2015

(30) Foreign Application Priority Data

Nov. 29, 2013 (KR) .................. 10-2013-0147576

(51) Int. Cl.
*G01N 15/06* (2006.01)
*G01N 21/53* (2006.01)
*G01N 15/02* (2006.01)
*G01N 33/00* (2006.01)
*G01N 15/00* (2006.01)

(52) U.S. Cl.
CPC ......... *G01N 15/0205* (2013.01); *G01N 15/06* (2013.01); *G01N 21/53* (2013.01); *G01N 33/0036* (2013.01); *G01N 2015/0046* (2013.01); *G01N 2015/0088* (2013.01); *G01N 2015/0693* (2013.01); *G01N 2201/0221* (2013.01)

(58) Field of Classification Search
USPC .................................................. 356/335–344
See application file for complete search history.

(56) References Cited

U.S. PATENT DOCUMENTS

| 3,499,159 | A | * | 3/1970 | Carrier | G01N 15/0205 250/225 |
| 3,788,742 | A | * | 1/1974 | Garbuny | G01N 21/39 356/218 |
| 5,298,751 | A | * | 3/1994 | Fee | G01N 21/3518 250/338.5 |
| 5,317,156 | A | * | 5/1994 | Cooper | G01N 21/39 250/339.13 |
| 5,373,160 | A | * | 12/1994 | Taylor | G01N 21/39 250/338.5 |
| 5,416,580 | A | * | 5/1995 | Trainer | G01N 15/0211 356/336 |
| 5,451,787 | A | * | 9/1995 | Taylor | G01N 21/39 250/338.5 |

(Continued)

FOREIGN PATENT DOCUMENTS

KR 1020010103916 A 11/2001

*Primary Examiner* — Tri Ton
*Assistant Examiner* — Jarreas C Underwood
(74) *Attorney, Agent, or Firm* — Perkins Coie LLP

(57) ABSTRACT

A portable apparatus for estimating air quality is provided. The portable apparatus includes a light source unit suitable for emitting incident light having a predetermined wavelength toward air to generate scattered light which is reflected by particles in the air, a light detection unit suitable for collecting information on the scattered light, and an arithmetic unit suitable for analyzing the information on the scattered light which is collected by the light detection unit. The arithmetic unit generates information on a size and a concentration of the particles in the air. Related methods are also provided.

14 Claims, 6 Drawing Sheets

(56) References Cited

U.S. PATENT DOCUMENTS

| | | | | |
|---|---|---|---|---|
| 5,540,494 A * | 7/1996 | Purvis, Jr. | ........... | G01N 15/0211 |
| | | | | 356/336 |
| 5,986,555 A * | 11/1999 | Hamburger | ............ | G01N 21/53 |
| | | | | 116/214 |
| 6,542,831 B1 * | 4/2003 | Moosmuller | .......... | G01N 21/33 |
| | | | | 702/24 |
| 6,885,440 B2 * | 4/2005 | Silcott | ................ | G01N 15/0205 |
| | | | | 250/492.1 |
| 7,100,423 B2 * | 9/2006 | Trenholm | .............. | G01N 15/02 |
| | | | | 73/28.02 |
| 7,132,657 B2 * | 11/2006 | Smith | ................ | G01N 21/3504 |
| | | | | 250/339.13 |
| 7,302,313 B2 * | 11/2007 | Sharp | ....................... | G01N 1/26 |
| | | | | 700/275 |
| 7,990,525 B2 * | 8/2011 | Kanda | ............... | G01N 15/1429 |
| | | | | 356/73 |
| 8,154,723 B2 * | 4/2012 | Fu | ..................... | G01N 15/0205 |
| | | | | 356/335 |

\* cited by examiner

PORTABLE APPARATUS FOR ESTIMATING AIR QUALITY AND METHODS OF OPERATING THE SAME

CROSS-REFERENCE TO RELATED APPLICATIONS

This patent document claims priority from and the benefits of Korean Patent Application No. 10-2013-0147576, filed on Nov. 29, 2013, the entirety of which is incorporated herein by reference.

TECHNICAL FIELD

The technology disclosed in this patent document relates to portable apparatuses for estimating the air quality and methods of operating the same.

BACKGROUND

Recently, air pollution has been seriously increased by contaminated materials or fine particles generated due to the industrial development. For example, a heavy metal content in the air has been increased to injure human health. Further, even the inside air of buildings or houses is also contaminated by fine dust, formaldehyde, or harmful bacteria or the like. The contaminated air may cause a sick building syndrome relating to nasal stuffiness, xerophthalmia, throat pain, sneeze, or physical fatigue or the like.

SUMMARY

Examples of implementations of the disclosed technology include portable apparatuses for estimating air quality in addition to methods of operating the same.

In one aspect, a portable apparatus for estimating air quality includes a light source unit to emit incident light having a predetermined wavelength toward air. The emitted incident light is scattered by particles in the air to generate scattered light. The portable apparatus includes a light detection unit to collect information on the scattered light. The portable apparatus includes an arithmetic unit to analyze the collected information on the scattered light and provide air quality indicator information including a size and a concentration of the particles in the air.

The portable apparatus can be implemented in various ways to include one or more of the following features. The arithmetic unit can perform an arithmetic operation using an equation including variables "r", "$\lambda$", "$n_0$" and "$\theta$". The variable "r" represents a mean value of distances between the particles and the light detection unit, the variable "$\lambda$," represents a wavelength of the scattered light, the variable "$n_0$" represents a refractive index of the air in a target space including the particles, and the variable "$\theta$" represents an angle between the incident light and the scattered light. The equation can include a first scattered light detection equation and a second scattered light detection equation. The first scattered light detection equation can be expressed by the following equation:

$$\frac{I}{I_0} = \frac{64\pi^4 n_0^2 a^6}{9\lambda^4 r^2}\left(\frac{dn_0}{d\varphi}\right)^2 (1 + (\cos\theta)^2).$$

The second scattered light detection equation can be expressed by the following equation:

$$g^2(\theta; \tau) = 1 + \beta\left[\exp\left(-\left(\frac{4\pi n_0}{\lambda}\sin\left(\frac{\theta}{2}\right)\right)^2 D\tau\right)\right]^2$$

where, $$D = \frac{k_B T}{6\eta a}(1 - 1.976\varphi).$$

"I" represents intensity of the scattered light, "$I_0$" represents intensity of the incident light, "a" represents a diameter of the particles, "$\varphi$" represents a volume percentage of the particles in the target space, "$\beta$" represents a correlation term, "$k_B$" represents a Boltzmann constant, "$\eta$" represents an intrinsic viscosity of the air in the target space, "$\tau$" represents a step time, "g($\theta$; $\tau$)" represents an autocorrelation function, "D" represents a diffusion coefficient of the particles in the target space, and "T" represents an absolute temperature of the air in the target space. The light source unit and the light detection unit can be disposed at opposite sides of the portable apparatus. The portable apparatus can include a detection conduit disposed between the light source unit and the light detection unit to allow generation of the scattered light in the detection conduit. The light source unit and the light detection unit can be disposed to be adjacent to each other. The portable apparatus can include a control unit to control operations of the light source unit and the light detection unit; and a display unit to display air quality indicator information produced by the arithmetic unit.

In another aspect, a portable apparatus for estimating air quality includes an inspection part and a production part that is attachable to and detachable from the inspection part. The inspection part includes a light source unit to emit light having a predetermined wavelength toward air. The emitted light is scattered by particles in the air to generate scattered light and a light detection unit configured to detect the scattered light. The production part includes a control unit to control the light source unit and the light detection unit and an arithmetic unit to analyze information on the scattered light detected by the light detection unit.

The portable apparatus can be implemented in various ways to include one or more of the following features. The arithmetic unit can provide air quality indicator information including a size and a concentration of the particles in the air and the production part can include a communication unit to transmit the air quality indicator information to an external device. The production part can be installed in a personal digital assistant (PDA), a portable computer, a wireless phone, a mobile phone, or a smart phone. The production part can be disposed in a portable terminal device to control operations of the inspection part using application programs loaded in the portable terminal device.

In another aspect, a method of operating a portable apparatus for estimating the air quality includes emitting incident light having a predetermined wavelength toward air. The emitted incident light is scattered by particles in the air to generate a scattered light. Information on scattered light is collected. The information on the scattered light is analyzed to produce air quality indicator information including a size and a concentration of the particles in the air.

The method can be implemented in various ways to include one or more of the following features. Analyzing the collected information on the scattered light can include performing an arithmetic operation using an equation including variables "r", "λ", "n₀" and "θ". The variable "r" represents a mean value of distances between the particles and the light detection unit, the variable "λ" represents a wavelength of the scattered light, the variable "$n_0$" represents a refractive index of the air in a target space including the particles, and the variable "θ" represents an angle between the incident light and the scattered light. The equation can include a first scattered light detection equation and a second scattered light detection equation. The first scattered light detection equation can be expressed by the following equation:

$$\frac{I}{I_0} = \frac{64\pi^4 n_0^2 a^6}{9\lambda^4 r^2} \left(\frac{dn_0}{d\varphi}\right)^2 (1 + (\cos\theta)^2)$$

wherein the second scattered light detection equation is expressed by the following equation:

$$g^2(\theta; \tau) = 1 + \beta \left[\exp\left(-\left(\frac{4\pi n_0}{\lambda}\sin\left(\frac{\theta}{2}\right)\right)^2 D\tau\right)\right]^2$$

$$\text{where, } D = \frac{k_B T}{6\eta a}(1 - 1.976\varphi)$$

wherein, "I" represents intensity of the scattered light, "$I_0$" represents intensity of the incident light, "a" represents a diameter of the particles, "φ" represents a volume percentage of the particles in the target space, "β" represents a correlation term, "$k_B$" represents a Boltzmann constant, "η" represents an intrinsic viscosity of the air in the target space, "τ" represents a step time, "g(θ; τ)" represents an autocorrelation function, "D" represents a diffusion coefficient of the particles in the target space, and "T" represents an absolute temperature of the air in the target space. The method can include displaying the air quality indicator information. The method can include transmitting the air quality indicator information to an external communication device.

In another aspect, a portable terminal device used for estimating the air quality is described. The portable terminal device includes a communication unit to receive information on scattered light indicative of environmental conditions of particles in air surrounding the communication unit. The portable terminal device includes a processor to analyze the received information on the scattered light using a predetermined algorithm to provide air quality indicator information. The air quality indicator information includes a size and a concentration of the particles in the air.

BRIEF DESCRIPTION OF THE DRAWINGS

Embodiments of the present disclosure will become more apparent in view of the attached drawings and accompanying detailed description, in which.

DETAILED DESCRIPTION

Figure 1:
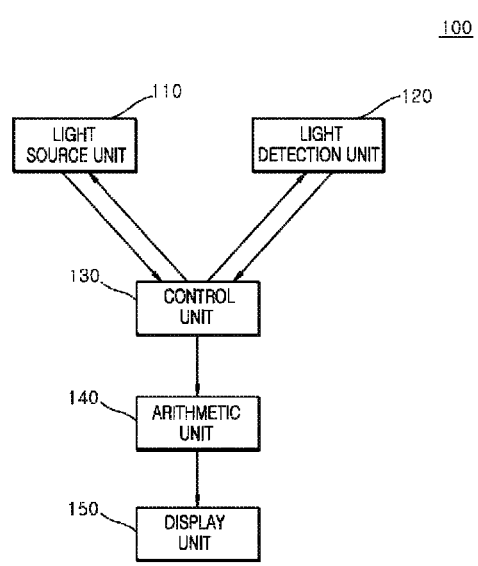
FIG. 1 is a block diagram illustrating an exemplary portable apparatus for estimating the air quality according to a first embodiment of the present disclosure.

These days, as many people raise concerns about the air pollution, it is desirable to obtain information on the environment conditions such as air pollution. Environmental information such as air pollution information available from the mass media tends to be based on data measured in specific regions at specific times. Because there are people living in various regions around the world in different time zones, it may be difficult to understand environmental conditions suitable for each person by using environmental information provided by the mass media. Due to the above and other reasons, it is desirable to make air pollution information at different times and different regions available. The technology disclosed in this patent document provides for a portable apparatus for estimating the air quality which can directly and easily measure the quality of air around each user at any time.

Certain terms in this patent document such as first, second, third etc. are merely used to provide labels for various elements, and the labels do not limit the scope of the labeled elements. These labeling terms are only used to distinguish one element from another element, and the labeling terms do not specify an order or a temporal relationship among the labeled elements.

It will also be understood that when an element is referred to as being located "under", "beneath," "below", "lower," "on", "over", "above," "upper", "side" or "aside" another element, the element can be directly contact the other element, or at least one intervening element may also be present between the elements. Accordingly, the terms such as "under", "beneath," "below", "lower," "on", "over", "above," "upper", "side" "aside" and the like which are used for the purpose of describing various specific examples or implementations only and are not intended to limit the scope of the scope of the description for the underlying technology.

It will be further understood that the terms "comprises", "comprising,", "includes" and/or "including", when used in this patent document, specify the presence of stated features, integers, steps, operations, elements, and/or components, but do not preclude the presence or addition of one or more other features, integers, steps, operations, elements, components, and/or groups thereof. Like reference numerals refer to like elements throughout the specification.

The examples of implementations of the disclosed technology include portable apparatuses for estimating the air quality, which are capable of easily measuring the quality of air around each user. In various aspects and examples, the portable apparatuses for estimating the air quality may employ a light emitting diode (LED) as a light source to reduce the weight of the portable apparatuses. In one aspect, an LED emitting ultraviolet rays, wavelengths of which are shorter than wavelengths of visible rays, may be used as the light source to react with contaminated particles having fine sizes. In addition, the portable apparatuses for estimating the air quality may employ a light detection unit that detects the light scattered by the contaminated particles to measure properties of the contaminated particles such as sizes or concentrations of the contaminated particles.

FIG. 1 is a block diagram illustrating an exemplary portable apparatus 100 for estimating the air quality according to one aspect of the disclosed technology. Referring to FIG. 1, the portable apparatus 100 may include a light source unit 110 and a light detection unit 120. The portable apparatus 100 may further include a control unit 130, an arithmetic unit 140 and a display unit 150.

The light source unit 110 may emit light with a predetermined wavelength that travels toward or directed to air in a target space. For example, the light source unit 110 may include at least one LED acting as a light source. The LED can be readily installed in the portable apparatus 100 because the LED is small and light. The LED may provide rays having a monochromic wavelength, for example, rays having a single wavelength within a range of a full width at half maximum (FWHM). In some implementations, the light source unit 110 may include an LED that emits ultraviolet (UV) rays, visible rays, infrared (IR) rays, or more than one wavelengths. For example, the light source unit 110 may include an LED that emits UV rays having a wavelength of about 300 nanometers to about 400 nanometers.

The light emitted from the light source unit 110 may be scattered by contaminated particles in air to generate scattered light, and the scattered light may be detected by the light detection unit 120. The scattered light may be generated by or consistent with Rayleigh scattering or Mie scattering.

In general, the Rayleigh scattering may occur when a size of a given particle is less than a wavelength of incident light colliding with the particles. In the Rayleigh scattering, the intensity of the scattered light may be inversely proportional to a four square value of a wavelength of the incident light. The Mie scattering may occur when a size of a given particle is almost equal to a wavelength of incident light colliding with the particles. In the Mie scattering, the intensity of the scattered light may be inversely proportional to a wavelength of the incident light. Accordingly, the Rayleigh scattering may be useful in detecting fine particles that have sizes which are less than a wavelength of the incident light colliding with the fine particles.

In some embodiments, UV rays having a short wavelength, which is less than wavelengths of visible rays, may be used as the incident light to detect the scattered light generated by or based on the Rayleigh scattering. In such a case, fine contaminant in the air may be readily detected or identified.

The light detection unit 120 may detect the fine particles distributed in the air at the target space and may provide to the control unit 130 information on properties of the particles, for example, sizes and concentrations of the fine particles in the air.

The control unit 130 is in communication with the light source unit 110 and the light detection unit to control operations of the light source unit 110 and the light detection unit 120. In some implementations, the control unit 130 may adjust the timing that the light source unit 110 emits the incident light into the air and may control a light receiving operation of the light detection unit 120 to be in synchronization with the timing of the emission of the incident light from the light source unit 110.

The arithmetic unit 140 is in communication with control unit 130 to receive data from the light detection unit 120 through the control unit 130. The arithmetic unit 140 may produce information on properties of the particles, for example, sizes and concentrations of the particles in the air, based on data of the scattered light detected by the light detection unit 120. The arithmetic unit 140 may include a calculation device for calculating the sizes and concentrations of the particles in the air.

The display unit 150 is in communication with the arithmetic unit 140, the control unit 130, the light source unit 110 and the light detection unit 120 through the arithmetic unit 140 and the control unit 130 to obtain data and information regarding all of the units 110, 120, 120 and 140 in the portable apparatus 100. The display unit 150 may display the received information about the light source unit 110, the light detection unit 120, the control unit 130, and the arithmetic unit 140 including the operation statuses of the light source unit 110, the light detection unit 120, and the control unit 130. In some implementations, the display unit 150 may display information on the air contamination which is calculated by the arithmetic unit 140. In some implementations, the display unit 150 may display information on various properties of the particles, for example, sizes and concentrations of the particles in the air, which are calculated by the arithmetic unit 140.

Figure 2:
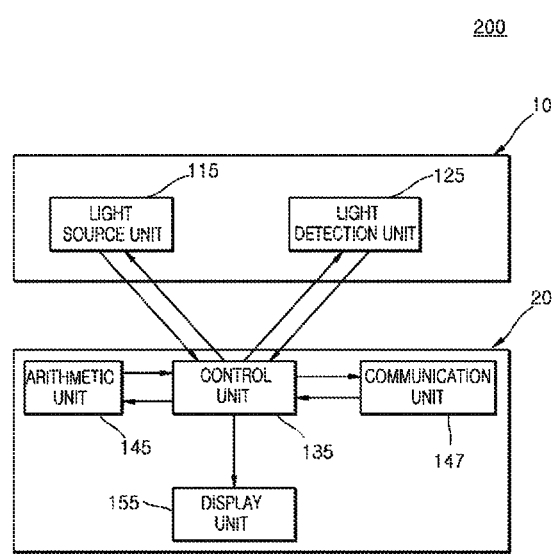
FIG. 2 is a block diagram illustrating an exemplary portable terminal device according to a second embodiment of the present disclosure.

FIG. 2 is a block diagram illustrating an exemplary portable terminal device 200 for estimating the air quality according to another aspect of the present disclosure. Referring to FIG. 2, the portable terminal device 200 includes two different body portions. For example, the portable terminal device 200 may include an inspection part 10 corresponding to a first body portion and a production part 20 corresponding to a second body portion. The first and second body portions may be combinable and separable from each other.

The inspection part 10 may include a light source unit 115 and a light detection unit 125. The light source unit 115 may emit light that travels toward or is directed to a target space filled with air and has a predetermined wavelength. The light source unit 115 may employ an LED as a light source. The LED can be readily installed in the portable terminal device 200 because the LED is small and light. The LED may provide rays having a monochromic wavelength, for example, rays having a single wavelength within a range of a full width at half maximum (FWHM). In some implementations, the light source unit 115 may include an LED that emits UV rays, visible rays, IR rays, or multiple wavelengths. For example, the light source unit 115 may include an LED that emits UV rays having a wavelength of about 300 nanometers to about 400 nanometers.

The light emitted from the light source unit 115 may be reflected or scattered by contaminated particles in the air to generate scattered light, and the scattered light may be detected by the light detection unit 125. The scattered light may be generated by Rayleigh scattering or Mie scattering. The light detection unit 125 may detect the fine particles distributed in the air and may provide to a control unit 135 information on properties of the particles, for example, sizes and concentrations of the fine particles in the air.

The production part 20 may include the control unit 135, an arithmetic unit 145, a communication unit 147 and a display unit 155. The production part 20 is in communication with the inspection part 10 by having the control unit 135 in communication with the light source 115 and the light detection unit 125. The control unit 135 may control operations of the light source unit 115 and the light detection unit 125. The arithmetic unit 145 is in communication with the control unit 135 and receives information regarding the light source unit 115 and the light detection unit 125. The arithmetic unit 145 may produce information on properties of the particles in the air, for example, sizes and concentrations of the particles in the air, based on data of the scattered light detected by the light detection unit 125. The arithmetic unit 145 may include a calculation device for calculating the sizes and concentrations of the particles in the air.

The communication unit 147 is in communication with the control unit 135 and may transmit the information on the detected contamination in the air produced by the arithmetic unit 145 to a communication medium such as another portable apparatus or a base station by wireless or cable communication. Alternatively, the communication unit 147 may receive the information on the contamination in the air from another portable apparatus or a base station by wireless or cable communication.

The display unit 155 is in communication with the control unit 135, and through its communication with the control unit 135, the display unit can receive information regarding the light source unit 115, the light detection unit 125, the arithmetic unit 145, the control unit 135 and the communication unit 147. The display unit 155 may display the received information including the operation statuses of the light source unit 115, the light detection unit 125, the control unit 135, the arithmetic unit 145 and the communication unit 147. Moreover, the display unit 155 may display information on the air contamination which is calculated by the arithmetic unit 145. In some implementations, the display unit 155 may display information on the sizes and concentrations of the particles in the air, which are calculated by the arithmetic unit 145.

In some embodiments, the display unit 155 may include a touch input device. The touch input device may receive user's input commands for operating the light source unit 115, the light detection unit 125, the control unit 135, the arithmetic unit 145 or the communication unit 147.

According to some embodiments, the production part 20 may be installed in a portable terminal device, such as the portable terminal device 200 for estimating the air quality. The portable terminal device may be or include a portable electronic system, for example, a personal digital assistant (PDA), a portable computer, a wireless phone, a mobile phone or a smart phone.

In some implementations, the operations of the production part 20 may be carried out by elements of the portable terminal device. For example, when the portable terminal device includes a processor, a communication unit, and a multimedia unit, and a touch input unit, the operations of the control unit 135, the arithmetic unit 145, the communication unit 147 and the display unit 155, which are included in the production part 20, may correspond to those of a processor, a communication unit, a multimedia unit and a touch input unit. In such a case, operations of the control unit 135, the arithmetic unit 145, the communication unit 147 and the display unit 155 may be controlled by application programs executed in the processor.

The inspection part 10 corresponding to a first body may be prepared independently from the production part 20 corresponding to a second body and then combined with the production part 20 to perform the operations for estimating an air pollution. A user can control the inspection part 10 by installing an application program in his or her portable terminal device which corresponds to the second body.

Figure 3:
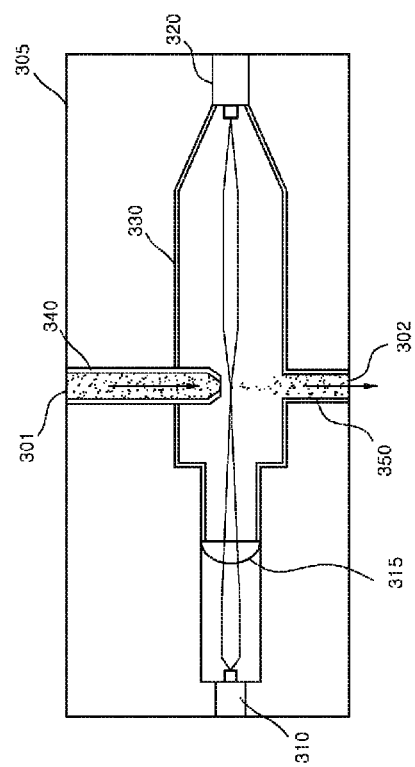
FIG. 3 is a cross-sectional view illustrating a light source unit and a light detection unit included in an exemplary portable apparatus for estimating the air quality according to an embodiment.

FIG. 3 is a cross-sectional view illustrating a light source unit 310 and a light detection unit 320 included in a portable apparatus for estimating the air quality according to one aspect. The light source unit 310 may have substantially the same configuration as the light source unit 110 or the light source unit 115 described with reference to FIG. 1 or 2, and the light detection unit 320 may have substantially the same configuration as the light detection unit 120 or the light detection unit 125 described with reference to FIG. 1 or 2.

As illustrated in FIG. 3, the light source unit 310 and the light detection unit 320 may be disposed in a body portion 305. For example, the light source unit 310 and the light detection unit 320 may be located at opposite sides of the body portion 305 to face each other. The body portion 305 may include an air inlet 301 and an air outlet 302. A detection conduit 330 may be disposed between the light source unit 310 and the light detection unit 320. Light emitted from the light source unit 310 may collide with air particles in the detection conduit 330 to generate scattered light, and the scattered light may be detected by the light detection unit 320.

An inflow conduit 340 may be disposed between the air inlet 301 and the detection conduit 330, and outside air may be introduced into the detection conduit 330 through the inflow conduit 340. An exhaust conduit 350 may be disposed between the air outlet 302 and the detection conduit 330, and the detected air in the detection conduit 330 may be vented out through the exhaust conduit 350.

An optical lens 315 is provided to focus the light emitted from the light source unit 310. In implementations, the optical lens 315 may be disposed at an end of the detection conduit 330 opposite to the light detection unit 320. The focused light may be introduced into the detection conduit 330. The scattered light generated by the air particles in the detection conduit 330 may be irradiated onto the light detection unit 320 at a predetermined scattering angle.

Figure 4:
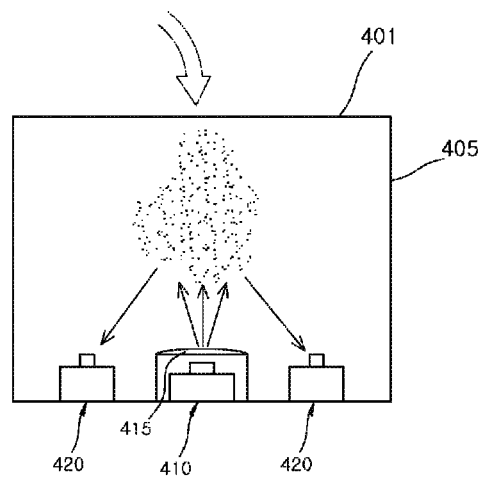
FIG. 4 is a cross-sectional view illustrating a light source unit and a light detection unit included in an exemplary portable apparatus for estimating air quality according to another embodiment.

FIG. 4 is a cross-sectional view illustrating a light source unit 410 and a light detection unit 420 included in a portable apparatus for estimating air quality according to another aspect. The light source unit 410 may have substantially the same configuration as the light source unit 110 or the light source unit 115 described with reference to FIG. 1 or 2, and the light detection unit 420 may have substantially the same configuration as the light detection unit 120 or the light detection unit 125 described with reference to FIG. 1 or 2.

The light source unit 410 and the light detection unit 420 may be disposed to be adjacent to each other in a body portion 405. Air may be introduced into the body portion 405 through an air inlet 401 and may be supplied onto the light source unit 410 and the light detection unit 420. The light source unit 410 may emit light toward the air introduced into the body portion 405. The light emitted from the light source unit 410 may collide with particles in the air to generate scattered light, and the scattered light may be detected by the light detection unit 420.

An optical lens 415 may be disposed on the light source unit 410 to focus the light emitted from the light source unit 410. Accordingly, the focused light may travel toward the air introduced into the body portion 405.

The light detection unit 420 may be disposed on a side of the light source unit 410 to receive the scattered light which is reflected by particles in the air. Although FIG. 4 illustrates an example in which two light detection units 420 are disposed at both sides of the light source unit 410, other implementations may include different numbers of the light detection unit 420. For example, a single light detection unit 420 may be disposed at one side of the light source unit 410.

Figure 5:
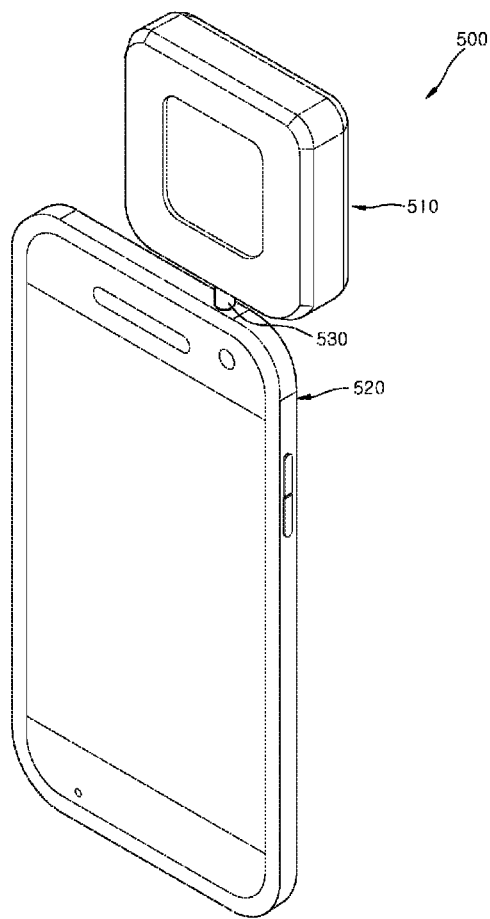
FIG. 5 is a schematic view illustrating an exemplary mobile system according to an embodiment.

FIG. 5 is a schematic view illustrating a mobile system 500 according to an embodiment. The mobile system 500 shows an example in which the portable terminal device 200 illustrated in FIG. 2 is employed.

The mobile system 500 may include an inspection device 510 and a terminal device 520. The inspection device 510 may have substantially the same configuration as the inspection part 10 described with reference to FIG. 2, and the terminal device 520 may have substantially the same configuration as the production part 20 described with reference to FIG. 2.

A connector 530 may allow the inspection device 510 to combine with or connect to the terminal device 520. The terminal device 520 may be or include an electronic system, for example, a PDA, a portable computer, a wireless phone, a mobile phone or a smart phone. A user may purchase only the inspection device 510 and readily measure environmental information such as a contamination degree of air around the user by connecting the inspection device 510 to the user's terminal device 520.

An exemplary principle of measuring the air quality using a light source unit and a light detection unit included in a portable apparatus are described. Light emitted from the light source unit may collide with air particles to generate scattered light, and the scattered light may be detected using different modes including a static light scattering mode and a dynamic light scattering mode.

Figure 6:
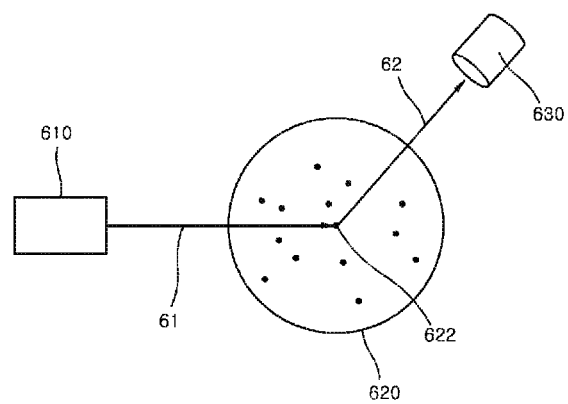
FIG. 6 is a schematic diagram illustrating an exemplary method of detecting scattered light generated in a portable apparatus for estimating the air quality according to an embodiment.

FIG. 6 is a schematic diagram illustrating a method of detecting scattered light generated in a portable apparatus for estimating the air quality according to an embodiment. Referring to FIG. 6, incident light 61 emitted from a light source unit 610 may collide with particles in a target space 620 to generate scattered light 62, and the scattered light 62 may be irradiated onto a light detection unit 630.

First, in the static light scattering mode, the intensity of scattered light I to incident light $I_0$ can be expressed by the following equation 1.

$$\frac{I}{I_0} = \frac{64\pi^4 n_0^2 a^6}{9\lambda^4 r^2} \left(\frac{dn_0}{d\varphi}\right)^2 (1 + (\cos\theta)^2) \quad (1)$$

wherein, "$n_0$" represents a refractive index of air in the target space 620 including the particles, "a" represents a diameter of the particles in the target space 620, "r" represents a mean value of distances between the particles and the light detection unit 630, "λ" represents a wavelength of the scattered light 62, "φ" represents a volume percentage of the particles in the target space 620, and "θ" represents an angle between the incident light 61 and the scattered light 62.

In the equation 1, "$n_0$", "r", "λ" and "θ" may be known values, and "$I/I_0$" may be measured and obtained by a static light scattering mode experiment. Thus, a relational expression between a particle diameter "a" and a ratio of variation of the refractive index of the air to variation of the volume percentage of the particles "($dn_0/d\varphi$)" may be obtained from the equation 1.

Meanwhile, in the dynamic light scattering mode, the intensity of the scattered light 62 can be obtained based on the elapse of a step time by using the following equations 2 and 3. In the dynamic light scattering mode, the incident light 61 having a pulse type may be irradiated toward the target space 620 at a point of time "t", and the intensity of the scattered light 62 may be detected and measured by the light detection unit 630 after the step time "τ" elapses from the point of time "t". In some embodiments, the step time "τ" may be equal to or less than 4 milliseconds.

$$g^2(q; \tau) = \frac{\langle I(t)I(t+\tau)\rangle}{\langle I(t)\rangle^2} \quad (2)$$

wherein, $q = \frac{4\pi n_0}{\lambda}\sin\frac{\theta}{2}$

-continued $$g^2(\theta; \tau) = 1 + \beta\left[\exp\left(-\left(\frac{4\pi n_0}{\lambda}\sin\left(\frac{\theta}{2}\right)\right)^2 D\tau\right)\right]^2 \quad (3)$$

wherein, $D = \frac{k_B T}{6\eta a}(1 - 1.976\varphi)$

In the equations 2 and 3, "g(q; τ)" and "g(θ; τ)" represent autocorrelation functions and the autocorrelation functions "g(q; τ)" and "g(θ; τ)" can be obtained by some experiments. In the equation 2, "q" in the autocorrelation function "g(q; τ)" represents a wave function, "I(t)" represents the intensity of the scattered light 62 at the point of time "t", "I(t+τ)" represents the intensity of the scattered light 62 at the point of time "t+τ", "<I(t)>" represents a mean value of the intensity of the scattered light 62 detected from the target space 620 at the point of time "t", "<I(t)I(t+τ)>" represents a mean value of products of the scattered light intensity "I(t)" at a point of time 't' and the scattered light intensity "I(t+τ)" at a point of time 't+τ'. In addition, "β" represents a correlation term, "$k_B$" represents a Boltzmann constant, "η" represents an intrinsic viscosity of the air in the target space 620, and "D" represents a diffusion coefficient of particles in the target space 620. Moreover, "T" represents an absolute temperature of the air in the target space 620.

In the equation 3, "$n_0$", "r", "λ" and "θ" may be known values and "τ" can be determined by a dynamic light scattering mode experiment. If a value of the autocorrelation function "g(q; τ)" obtained from the equation 2 is provided to the equation 3, a relational expression between the diameter "a" of the particles and the volume percentage "φ" of the particles in the target space 620 may be deduced.

Using the relational expression deduced from the equations 2 and 3, the diameter "a" and the volume percentage "φ" of the particles in the target space 620 can be produced. As such, environmental information, for example, the size and the concentration of the particles in the target space 620 may be obtained. "T" represents an absolute temperature of the air in the target space 620.

In order to execute the operations for calculating the information described above, the arithmetic unit 140 (or 145) illustrated in FIG. 1 (or 2) may include a storage device for storing information on the scattered light detected by the light detection unit 120 (or 125), an information operational device, and an air quality analysis device. The storage device may store the information on the scattered light obtained at a point of time "t". The information operational device may calculate a mean value of the intensity of the scattered light or may calculate a value of the autocorrelation function "g(q; τ)", based on the information on the scattered light. The air quality analysis device may analyze various characteristics of the particles, such as the size, distribution and concentration of the contaminated particles in the target space 620, based on the information calculated by the information analysis device. In one implementation, the air quality analysis device may evaluate the analyzed information on the contaminated particles to be consistent with actual environmental conditions. For example, the air quality analysis device may perform operations for removing noises included in the analyzed information on the contaminated particles and compensating the analyzed information in consideration of environmental temperature or environmental humidity. In one implementation, to perform the above described evaluating operations, calibration operations for comparing the measured or analyzed information with reference information and for correcting the measured or analyzed information may be periodically performed.

As described above, the portable apparatus according to the embodiment may operate in both the static and dynamic light scattering modes to analyze the scattering light. Thus, properties of the particles including a size and a concentration of particles in air contained in a target space may be accurately measured by using a relational formula between a diameter "a" of the particles and a volume percentage "φ" of the particles, which is obtained from the static and dynamic light scattering modes.

A light source unit may emit light having a predetermined wavelength toward air and the light emitted from the light source unit may collide with contaminated particles in the air to generate scattered light. The scattered light may be detected by a light detection unit, and information on properties including sizes and concentration of the contaminated particles may be produced based on data of the scattered light detected by the light detection unit.

If the light source unit and the light detection unit are combined with a portable terminal device, a user of the portable terminal device may readily measure and estimate environmental data including a contamination degree of air around the user.

Only a few embodiments, implementations and examples are described and other embodiments and implementations, and various enhancements and variations can be made based on what is described and illustrated in this document.

What is claimed is:

1. A portable apparatus for estimating air quality, the portable apparatus comprising:
   a light source configured to emit incident light having a predetermined wavelength toward air, the emitted incident light is scattered by particles in the air to generate scattered light;
   a light detector configured to detect the scattered light and collect information on the scattered light; and
   a calculator configured to analyze the collected information on the scattered light from the light detector and to provide air quality indicator information including a size and a concentration of the particles in the air;
   wherein the calculator is configured to perform an arithmetic operation using an equation including variables "r", "λ", "$n_0$" and "θ",
   wherein the variable "r" represents a mean value of distances between the particles and the light detector, the variable "λ" represents a wavelength of the scattered light, the variable "$n_0$" represents a refractive index of the air in a target space including the particles, and the variable "θ" represents an angle between the incident light and the scattered light,
   wherein the equation includes a first scattered light detection equation and a second scattered light detection equation;
   wherein the first scattered light detection equation is expressed by the following equation:

$$\frac{I}{I_0} = \frac{64\pi^4 n_0^2 a^6}{9\lambda^4 r^2} \left(\frac{dn_0}{d\varphi}\right)^2 (1 + (\cos\theta)^2),$$

wherein the second scattered light detection equation is expressed by the following equation:

$$g^2(\theta; \tau) = 1 + \beta\left[\exp\left(-\left(\frac{4\pi n_0}{\lambda}\sin\left(\frac{\theta}{2}\right)\right)^2 D\tau\right)\right]^2$$

$$\text{where, } D = \frac{k_B T}{6\eta a}(1 - 1.976\varphi),$$

wherein, "I" represents intensity of the scattered light, "$I_0$" represents intensity of the incident light, "a" represents a diameter of the particles, "φ" represents a volume percentage of the particles in the target space, "β" represents a correlation term "$k_B$" represents a Boltzmann constant, "η" represents an intrinsic viscosity of the air in the target space, "τ" represents a step time, "g(θ,τ)" represents an autocorrelation function, "D" represents a diffusion coefficient of the particles in the target space, and "T" represents an absolute temperature of the air in the target space.

2. The portable apparatus of claim 1,
   wherein the light source and the light detector are disposed at opposite sides of the portable apparatus; and
   wherein the portable apparatus further includes a detection conduit disposed between the light source and the light detector to allow generation of the scattered light in the detection conduit.

3. The portable apparatus of claim 1,
   wherein the light source and the light detector are disposed to be adjacent to each other.

4. The portable apparatus of claim 1, further comprising:
   a display configured to display air quality indicator information produced by the arithmetic unit.

5. The portable apparatus of claim 1, further comprising:
   a controller configured to control the light source and the light detector.

6. The portable apparatus of claim 5, further comprising:
   a transmitter configured to transmit the air quality indicator information to an external device.

7. The portable apparatus of claim 5, wherein the controller is installed in a personal digital assistant (PDA), a portable computer, a wireless phone, a mobile phone, or a smart phone.

8. The portable apparatus of claim 5,
   wherein the controller is disposed in a portable terminal device and is configured to control operations of the light source and the light detector using application programs loaded in the portable terminal device.

9. A method of operating a portable apparatus for estimating air quality, the method comprising:
   emitting incident light having a predetermined wavelength toward air, the emitted incident light is scattered by particles in the air to generate a scattered light;
   collecting information on scattered light;
   analyzing the collected information on the scattered light to produce air quality indicator information including a size and a concentration of the particles in the air,
   wherein the analyzing of the collected information on the scattered light includes performing an arithmetic operation using an equation including variables "r", "λ", "$n_0$" and "θ";
   wherein the variable "r" represents a mean value of distances between the particles and a light detector collecting information on the scattered light, the variable "λ" represents a wavelength of the scattered light, the variable "$n_0$" represents a refractive index of the air in a target space including the particles, and the variable "θ" represents an angle between the incident light and the scattered light, wherein the equation includes a first scattered light detection equation and a second scattered light detection equation;
wherein the first scattered light detection equation is expressed by the following equation;

$$\frac{I}{I_0} = \frac{64\pi^4 n_0^2 a^6}{9\lambda^4 r^2}\left(\frac{dn_0}{d\varphi}\right)^2 (1 + (\cos\theta)^2)$$

wherein the second scattered light detection equation is expressed by the following equation; and $$g^2(\theta; \tau) = 1 + \beta\left[\exp\left(-\left(\frac{4\pi n_0}{\lambda}\sin\left(\frac{\theta}{2}\right)\right)^2 D\tau\right)\right]^2$$

$$\text{where, } D = \frac{k_B T}{6\eta a}(1 - 1.976\varphi)$$

wherein, "I" represents intensity of the scattered light, "$I_0$" represents intensity of the incident light, "a" represents a diameter of the particles, "φ" represents a volume percentage of the particles in the target space, "β" represents a correlation term, "$k_B$" represents a Boltzmann constant, "η" represents an intrinsic viscosity of the air in the target space, "τ" represents a step time, "g(θ,τ)" represents an autocorrelation function, "D" represents a diffusion coefficient of the particles in the target space, and "T" represents an absolute temperature of the air in the target space.

10. The method of claim 9, further comprising displaying the air quality indicator information.

11. The method of claim 9, further comprising transmitting the air quality indicator information to an external communication device.

12. The portable apparatus of claim 1, wherein the calculator is disposed to be attachable to and detachable from the light source and the light detector.

13. The portable apparatus of claim 1, wherein the calculator is disposed in a portable terminal device and is configured to control operations of the light source and the light detector using application programs loaded in the portable terminal device.

14. The portable apparatus of claim 1, wherein the calculator is installed in a personal digital assistant (PDA), a portable computer, a wireless phone, a mobile phone, or a smart phone.

* * * * *